United States Patent [19]

Wass

[11] Patent Number: 4,528,840

[45] Date of Patent: Jul. 16, 1985

[54] HYDROSTATIC TEST STAND

[76] Inventor: Lloyd G. Wass, 1670 Blackhawk Cove, Eagan, Minn. 55123

[21] Appl. No.: 577,150

[22] Filed: Feb. 6, 1984

[51] Int. Cl.$^3$ .............................................. G01M 3/02
[52] U.S. Cl. ........................................ 73/37; 73/149; 73/49.4
[58] Field of Search ...................... 73/37, 149, 40.5 R, 73/49.1, 49.5, 49.4

[56] References Cited

U.S. PATENT DOCUMENTS

| | | | |
|---|---|---|---|
| 1,783,412 | 12/1930 | Crowe | 73/37 |
| 2,353,275 | 7/1944 | Clair | 73/37 |
| 2,539,843 | 1/1951 | Kerr | 73/37 |
| 2,652,717 | 9/1953 | Bush et al. | 73/40.5 R |
| 2,821,851 | 2/1958 | Daley | 73/37 |
| 3,151,478 | 10/1964 | Heldenbrand | 73/49.1 |
| 3,577,768 | 5/1971 | Aprill, Jr. | 73/40.5 R |
| 4,090,394 | 5/1978 | Herman et al. | 73/37 |

Primary Examiner—Stewart J. Levy
Assistant Examiner—Hezron E. Williams
Attorney, Agent, or Firm—Kinney & Lange

[57] ABSTRACT

A hydrostatic test stand provides proof-testing of pressure vessels by measuring the amount of total deformation and permanent deformation as a result of a hydrostatic pressure applied to the pressure vessel. The test stand includes a transfer cylinder (which contains a floating piston and a bias spring), first and second control valves, a graduated cylinder, a pressure sensor, an oil reservoir, a booster pump, a booster pump valve, and quick-connect couplings. The pressure vessel is filled with water and connected to the couplings. With all of the valves open, the piston is at the lower end of the cylinder, and water is used to fill a first volume above the piston and the fluid lines to the pressure vessel, as well as filling the graduated cylinder to a predetermined first level. The first control valve and the booster pump valve are then closed and the booster pump is operated to drive the piston upward by oil pressure until a predetermined pressure has been reached in the pressure vessel. The second control valve is then closed, and the booster pump valve and the first control valve are opened, thus permitting the piston to move downward to its home position, which draws liquid from the graduate cylinder into the transfer cylinder. The second control valve is then opened to allow the pressure vessel to contract and force water back into the graduate cylinder. By comparing the first level of water in the graduate cylinder with the second and third levels after the first and second control valves are opened, a measure of dynamic and static deformation of the pressure vessel is obtained.

8 Claims, 2 Drawing Figures

HYDROSTATIC TEST STAND

FIELD OF THE INVENTION

The present invention relates to proof-testing of pressure vessels used for containing gases under pressure. In particular, the present invention is an improved hydrostatic test stand and method for proof-testing of pressure vessels.

DESCRIPTION OF THE PRIOR ART

Portable pressure vessels which store gases under very high static fluid pressure are used to inflate life rafts carried by ocean-going ships and aircraft. An inflatable life raft offers the advantage of light-weigt and small size, and can be stored in its deflated condition for long periods of time when it is not needed. The pressurized inflation gas contained in the pressure vessel permits the inflatable life raft to be inflated rapidly when needed to form a large raft capable of holding relatively large numbers of people.

Another common use of portable pressure vessels is by fire departments which provide backpack air systems for fire fighters. The backpack includes one or more tanks containing air under pressure.

In both of these applications, and in others as well, such as portable fire extinguishers there is a need to refill the portable pressure vessel after it has once been used. It is very dangerous, however, to fill a pressure vessel, particularly one which may have been subjected to rough handling, without knowing whether the pressure vessel is in good condition and is capable of withstanding the static pressures to which it will be subjected. If the pressure vessel is not in good condition, the compressibility of the gas with which it is filled can cause an explosion. In the past, injuries and deaths have occurred when pressure vessels in poor condition have exploded while being filled with gas to a very high fluid pressure.

To ensure that an explosion will not occur when the pressure vessel is refilled, proof-testing of that pressure vessel is typically performed. This proof-testing uses an incompressible liquid, such as oil or water, rather than a compressible gas to apply a predetermined static pressure to the cylinder. An excessive expansion of the pressure vessel under the predetermined static pressure indicates that the pressure vessel is weak, and could explode if filled with gas. By using proof-testing, therefore, potentially unsafe pressure vessels can be identified and discarded. Only those pressure vessels which have passed the proof-testing are refilled.

In the past, the equipment used for proof-testing of pressure vessels of the type used for inflatable life rafts and backpack air systems for firefighters has been large, stationary, and extremely expensive. As a result, most facilities (such as shipyards and fire departments) which use portable pressure vessels do not maintain its own proof-testing facilities or equipment. Instead, the tanks are sent to a company having proof-testing equipment in order to have the proof-testing performed.

This arrangement has a number of inherent disadvantages. Sending the pressure vessels out for proof-testing is expensive, inconvenient and time-consuming. Because the proof-testing cannot be performed immediately and is expensive, there is a tendency to have proof-testing performed only at sporatic intervals.

Proof-testing can be performed using any liquid. In the past both oil and water have been used for proof-testing. The disadvantage of oil as the proof-testing liquid is that the interior of the pressure vessel is subjected to the oil, and it is very difficult to remove all the oil from the cylinder after proof-testing.

It is desirable to test with water rather than oil because air can be used to flush the system (including the pressure vessel) after proof-testing has been completed. The pressure vessel is permitted, therefore, to dry out before it is placed back in service, with no residual water left in the pressure vessel.

The disadvantage of using water for proof-testing is that it places special requirements upon the components of the system in order to avoid problems with corrosion. In the past, the proof-testing systems which use water have also used a totally stainless steel pump to avoid the corrosion problems. This results in very expensive proof-testing equipment.

SUMMARY OF THE INVENTION

The present invention is an improved hydrostatic test stand and method for proof-testing a pressure vessel such as a tank for an inflatable life raft or a backpack tank for firefighters. The present invention achieves the advantages of using water to pressurize the pressure vessel, without the corrosion problems which have in the past required the use of a stainless steel pump to pump the water. In the present invention, hydraulic fluid is pumped under pressure from a reservoir to a transfer cylinder. The pressure of the hydraulic fluid is transferred by the transfer cylinder to water, which is then supplied under pressure to the pressure vessel. As a result, the pressure vessel is only exposed to water, while the booster pump is exposed only to hydralic fluid.

The transfer cylinder has a bore in which a floating piston moves between first and second ends of the transfer cylinder. A first fluid passage is positioned at a first end of the transfer cylinder, and a second fluid passage is positioned at a second end of the transfer cylinder. A bias spring within the transfer cylinder applies a bias force to the piston which urges the piston toward a home position at the second end of the transfer cylinder. The first end of the transfer cylinder is connected through a first control valve to a graduated cylinder and through a second control valve and coupling means to a port of the pressure vessel. The second fluid passage is connected to the booster pump through a booster pump valve. A pressure sensor is connected to provide a measurement of pressure within the pressure vessel.

Proof-testing is performed by filling the pressure vessel with water and connecting the pressure vessel port to the coupling means. The first and second control valves and the booster pump valve are all open, and water is supplied through the graduated cylinder to fill a first volume of the transfer cylinder between the piston and the first end, the fluid lines, and the graduated cylinder, so that the starting level of the column of water within the graduated cylinder is at a predetermined first level. With all three valves open, the piston is in its home position at the second end of the transfer cylinder due to the bias force from the bias spring.

The first control valve and the booster pump valve are then closed, and the booster pump is started to pump oil from the reservoir through the booster pump valve (which operates as a one-way valve when it is closed) and into a second volume between the second end of the transfer cylinder and the piston. The pressure of the hydraulic fluid causes the piston to move toward the first end, thus displacing water from the first volume within the transfer cylinder, through the second control valve, and into the pressure vessel. The booster pump is operated until a predetermined pressure is indicated by the pressure sensor.

The second control valve is then closed, thus holding the water within the pressure vessel at the predetermined pressure. The booster pump valve is opened, and the first control valve is opened, thus permitting the water within the graduated cylinder to flow into the first volume as the bias spring moves the piston back to the home position at the second end. This forces the hydraulic fluid out of the second volume, through the booster pump valve and the booster pump, and into the reservoir.

When the piston has reached the home position, the column of water within the graduated cylinder has decreased to a second level. The difference between the first level and the second level represents the volume of water displaced from the transfer cylinder when the pressure vessel was pressurized to the predetermined pressure. Since all of the water displaced from the transfer cylinder was transferred to the pressure vessel, the difference between the first and second levels also represents the total volumetric expansion of the pressure vessel as it was pressurized to the predetermined pressure.

The second control valve is then opened, which permits the pressure vessel to contract and force water back through the second valve until pressure equilibrium is reached. Since the piston is at its home position and the first volume within the transfer cylinder is already filled with water, the excess water from the pressure vessel flows through the second control valve and then through the first control valve into the graduated cylinder. This results in an increase in the column of water within the graduated cylinder to a third level. The difference between the third level and the first level represents the permanent volumetric expansion of the pressure vessel as a result of its exposure to the predetermined pressure.

An excessive amount of deformation of the pressure vessel during proof-testing indicates that the walls of the pressur vessel are weak, and that the filling of the pressure vessel with gas could be hazardous.

DETAILED DESCRIPTION OF THE PREFERRED EMBODIMENTS

Figure 1:
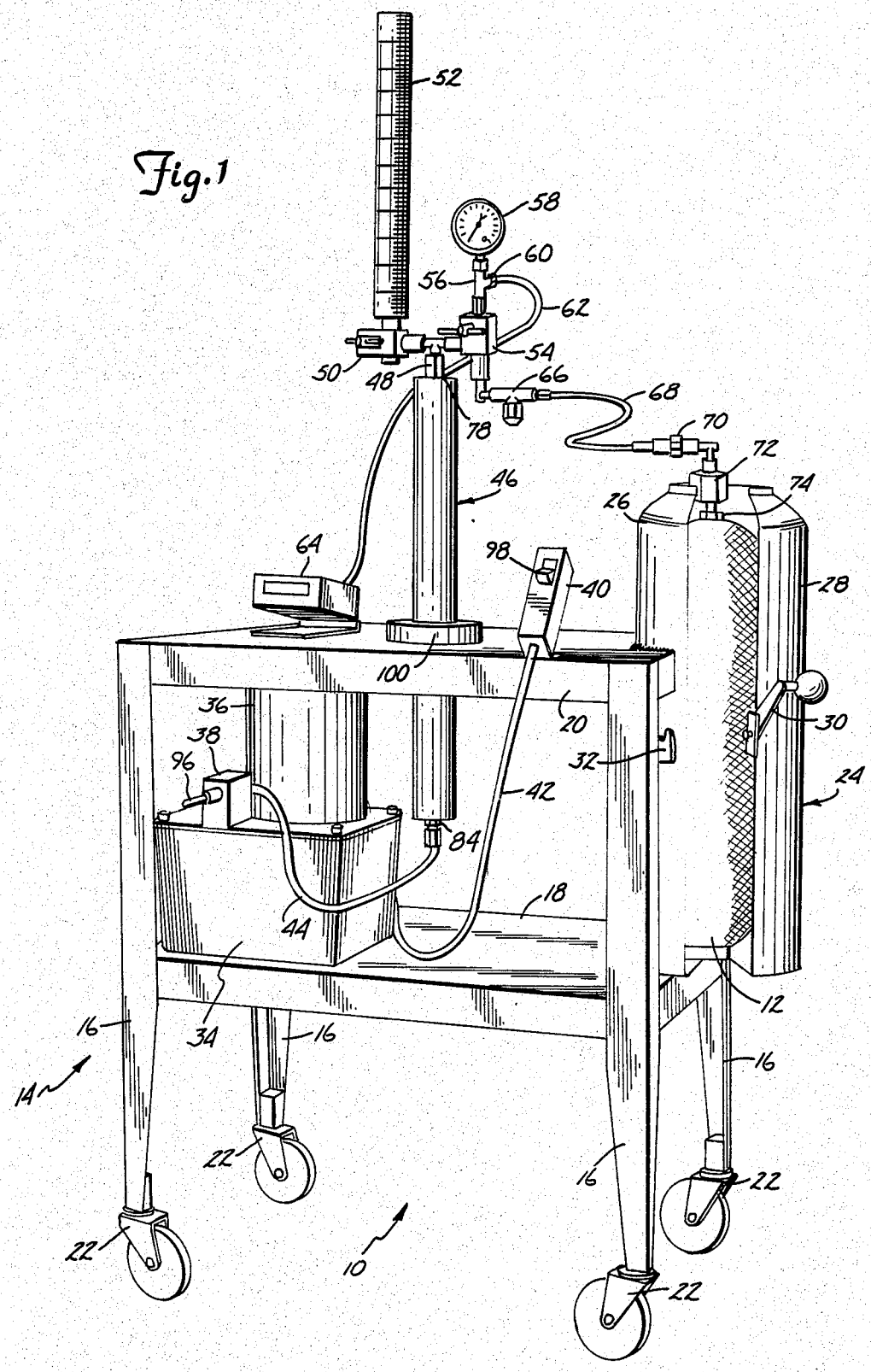
FIG. 1 is a perspective view of a preferred embodiment of the hydrostatic test stand of the present invention.
Figure 2:
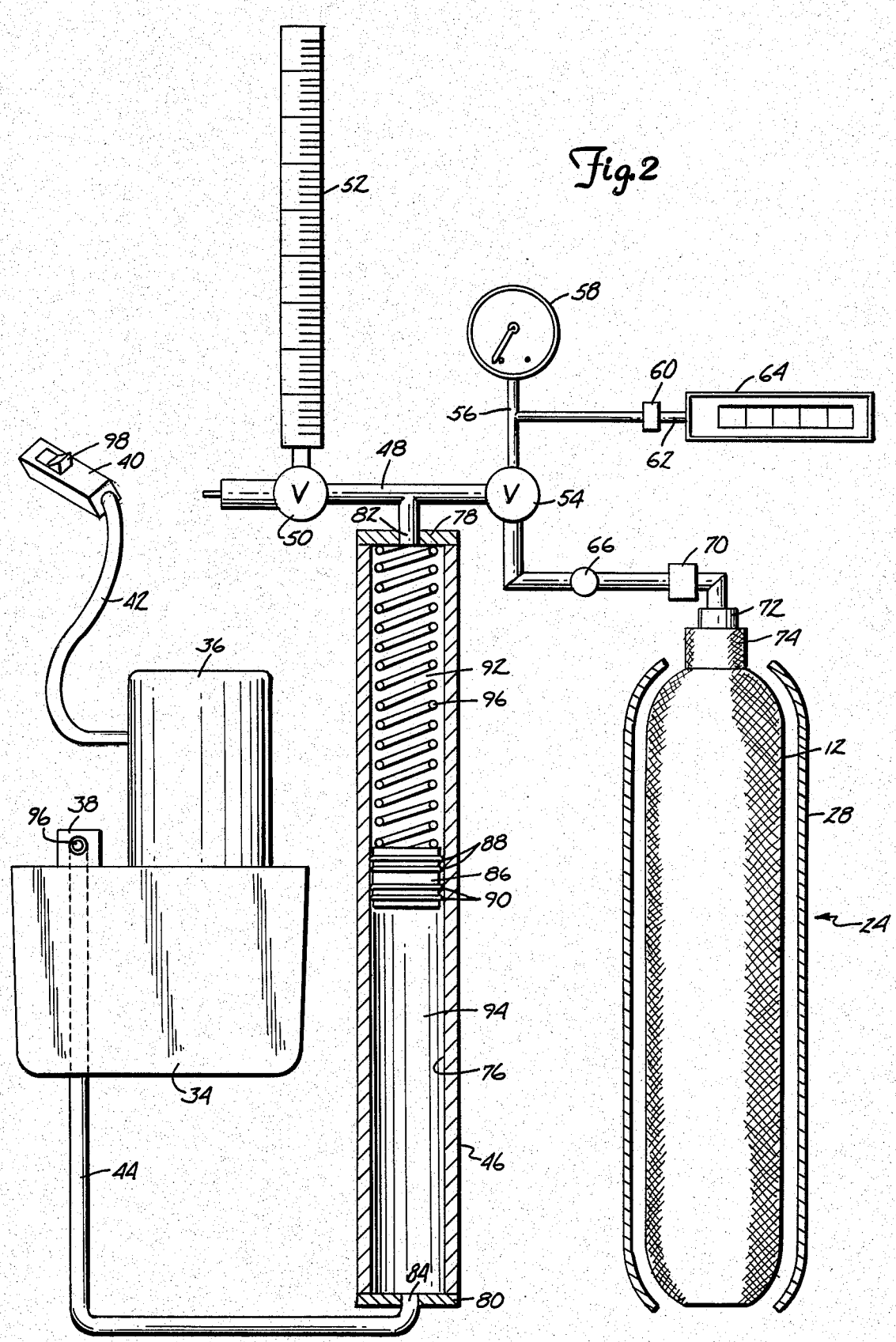
FIG. 2 is a schematic view of the hydrostatic test stand of FIG. 1.

As shown in FIGS. 1 and 2, hydrostatic test stand 10 of the present invention provides proof-testing of a pressure vessel 12, such as an air cylinder for an inflatable life raft. Hydrostatic test stand 10 is a lightweight, low cost, portable apparatus which, in the preferred embodiment shown in FIG. 1, is mounted on movable cart 14. This allows test stand 10 to be moved from place-to-place, as needed, and then moved to a storage location when not in use.

In the embodiment shown in FIG. 1, cart 14 has four legs 16, lower shelf 18, upper shelf 20, and caster wheels 22. Attached at one end of cart 14 is cage 24, into which pressure vessel 12 is inserted during testing. Cage 24 is formed by a pair of semi-cylindrical shells 26 and 28 which are connected together along one edge by hinged (not shown). Shell 26 is fixedly attached (for example by welding) to cart 14. When shell 28 is in the closed position, latch arm 30 (which is carried by shell 28) is lowered to engage latch hook 32 (which is attached to one of the legs 16) so as to hold cage 24 closed during testing.

Test stand 10 includes hydraulic fluid reservoir 34, electrical booster pump 36, booster pump valve 38, booster pump control 40, electrical cable 42, hydraulic fluid line 44, transfer cylinder 46, T connector 48, first control valve 50, graduated cylinder 52, second control valve 54, T connector 56, pressure gauge 58, electrical pressure sensor 60, cable 62, digital pressure monitor 64, filter 66, fluid line 68, and quick-connect couplings 70 and 72.

Transfer cylinder 46 converts hydraulic fluid pressure provided by booster pump 36 into water pressure which is supplied through second control valve 54, filter 66, fluid line 68 and quick-connect couplings 70 and 72 to port 74 of pressure vessel 12. As shown in FIG. 2, transfer cylinder 46 has an inner bore 76, a first end 78, and a second end 80. Fluid passage 82 in first end 78 is connected to T connector 48. Second fluid passage 84 in second end 80 is connected to fluid line 44.

Positioned within bore 76 of cylinder 46 is double-ended floating piston 86. At the upper end of piston 86, a pair of O-rings 88 are mounted. Similarly, a pair of O-rings 90 are mounted on the lower end of piston 86. Both pairs of O-rings 88 and 90 provide a sliding seal with bore 76.

In other embodiments of the present invention, O-rings 88 and 90 are replaced by cup rings which also perform a sealing and wiping action as piston 90 moves within bore 76. In either embodiment, it is important that the rings not only seal but also wipe clean the bore 76 as piston 86 moves within transfer cylinder 46. This is required because water fills first variable volume 92 between rings 88 and first end 78, and hydraulic fluid fills second variable volume 94 between rings 90 and second end 80. Rings 88 and 90 must clean bore 76 as piston 86 moves, so that there is no contamination of water in hydraulic fluid or hydraulic fluid in water. To achieve this wiping and cleaning action of rings 88 and 90, bore 76 has an extremely smooth surface, which is preferably a "16 micro-finish".

As also illustrated in FIG. 2, bias spring 96 is located within transfer cylinder 46 between first end 78 and piston 86. Bias spring 96 is preferably a compression coil spring which is shown in partially compressed condition in FIG. 2. Bias spring 96 applies a bias force to piston 86 which will return piston 86 to a home position adjacent second end 80. In this home position, first volume 92 is a maximum, and second volume 94 is a minimum.

In one preferred embodiment of the present invention, reservoir 34, booster pump 36, booster pump control valve 38, and control 40 are all a part of an OTC Power Team Series PE17 hydraulic power unit sold by Owatonna Tool Corporation of Owatonna, Minn. Booster pump valve 38 has a control lever 96 which selects an open or a closed position. When closed, booster pump valve 38 permits only one-way flow of fluid from booster pump 36 to transfer cylinder 46 through fluid line 44. When open, booster pump valve 38 permits reverse flow from volume 94 of transfer cylinder 46, through fluid line 44 and valve 38 back to reservoir 34.

Booster pump control 40 is a hand-held control with a spring-loaded rocker switch 98 which is normally biased to an OFF position. To run booster pump 36, rocker switch 98 must be held in the ON position.

As shown in FIG. 1, transfer cylinder 46 extends through top shelf 20 of cart 14, and is secured to top shelf 20 by mounting collar 100. T connector 48 is attached at first (upper) end 78 of transfer cylinder 46, so that T connector 48 and the apparatus connected to it are all supported above cart 14 by transfer cylinder 46.

T connector 48 has a leg connected to fluid passage 82 at first end 78 of transfer cylinder 46. First control valve 50 is connected to one arm and second control valve 54 is connected to the other arm of T connector 48. Valves 50 and 54 are preferably similar valves, which are capable of withstanding pressures to which pressure vessel 12 will be subjected during proof-testing.

When first control valve 50 is open, it provides communication between graduated cylinder 52 and T connector 48. When second control valve 54 is open, it provides fluid passage between T connector 48 and fluid line 68.

Pressure gauge 58 and electrical pressure sensor 60 are connected by T connector 56 to valve 54 in such a way that they are subjected to the same pressure as pressure vessel 12 when second control valve 54 is open. Gauge 58 provides a direct mechanical reading of fluid pressure, while electrical pressure sensor 60 provides electrical signals through cable 62 to digital pressure monitor 64, which converts those electrical signals to a digitally displayed pressure value. The purpose of both pressure gauge 58 and digital pressure monitor 64 is to provide the operator with an indication of the pressure level within pressure vessel 12, so that operation of booster pump 36 can be continued until a desired pressure level has been attained.

Before hydrostatic test stand 10 can be used, the trapped air must be purged from the fluid lines and couplings and from control valves 50 and 54. This purging process is as follows:

(1) Pressure vessel 12 is filled with water, quick-connect coupling 72 is attached to port 74, and pressure vessel 12 is placed within cage 24. Quick-connect coupling 70 is then connected to coupling 72, so that pressure vessel 12 is connected to test stand 10. Shell 28 of cage 24 is swung closed, and latch arm 30 is lowered into latch 32 to hold cage 24 closed.

(2) Control valves 50 and 54 and booster pump valve 38 are opened.

(3) Graduated cylinder 52 is filled with water until the column of water in graduated cylinder 52 reaches a predetermined first level is attained (usually the top of cylinder 52). Because bias spring 96 has biased piston 86 to its home position, sufficient water must be introduced into the system through graduated cylinder 52 to fill first volume 92 of transfer cylinder 46, as well as to fill various fluid passages of the system.

(4) First control valve 50 and booster pump valve 38 are closed.

(5) Booster pump 36 is started and hydraulic fluid is pumped from reservoir 34 through pump 36, valve 38 and line 44 into second volume 94 of transfer cylinder 46. The hydraulic fluid pressure drives piston 90 upward against the bias force from spring 96, thus forcing water out of fluid passage 82 at the top of cylinder 46 and through T connector 48, valve 54, filter 66, fluid line 68, and connectors 70 and 72 into pressure vessel 12. Booster pump 36 is run until a pressure of approximately 500 to 600 psi is reached. At this point, booster pump 36 is stopped, and the operator checks for any fluid leaks.

(6) First control valve 50 is then open slowly, which permits pressure vessel 12 to contract and force expansion the volume of water back through fluid line 68 and second control valve 54 and first control valve 50 into graduated cylinder 52. This flushes air from the system, and bubbles will appear in graduated cylinder 52.

(7) Booster pump valve 38 is opened, thus permitting the hydraulic fluid to return from second volume 94 to reservoir 34, and allowing piston 86 to move downward to its home position due to the bias force of bias spring 96.

(8) Steps (3), (4), (5) and (6) are repeated until no new bubbles appear in graduated cylinder 52.

At this point, the hydrostatic test stand 10 has been purged of trapped air, and is ready for a hydrostatic proof test cycle. The cycle begins with piston 86 in its home position, and with valves 38, 50 and 54 open.

(9) Graduated cylinder 52 is again filled to the first level, so that a known starting point is provided.

(10) First control valve 50 and booster pump valve 38 are closed.

(11) Booster pump 36 is started, and is permitted to run until a predetermined hydrostatic pressure is indicated by pressure gauge 58 and/or digital pressure monitor 64.

(12) Second control valve 54 is closed, thus capturing within pressure vessel 12 the water under pressure within vessel 12.

(13) Booster pump valve 38 is opened, which provides a return passage for the hydraulic fluid within second volume 94 back to reservoir 34. In addition, first control valve 50 is opened, which permits water from graduated cylinder 52 to flow through first control valve 50 and T connector 48 into first volume 92 as bias spring 96 forces piston 86 downward to its home position. When piston 86 has reached its home position, the first volume 92 is a maximum, and a second volume 94 is a minimum, and the column of water in graduated cylinder 52 is at a second level.

(14) The second level of the column of water within graduated cylinder 52 is noted. The difference between the first level and the second level (which is reached after booster valve pump 38 and first control valve 50 have been opened and piston 86 has returned to its home position) represents the total volumetric expansion of pressure vessel 12 due to the predetermined hydrostatic pressure.

(15) Second control valve 54 is opened, thus permitting the water under pressure within pressure vessel 12 to flow back through line 68 and second control valve 54 to T connector 48. Since piston 86 is already in its home position and first volume 92 is already at a maximum, the excess water which flows back from pressure vessel 12 as pressure vessel 12 contracts is forced into graduated cylinder 52, thus raising the column of water within graduated cylinder 52 to a third level.

(16) After the system has equilibrated, the third level of the column of water within graduated cylinder 52 is noted. The difference between the first level and the third level represents the permanent deformation of pressure vessel 12 which has occurred as a result of being subjected to the predetermined hydrostatic pressure during proof-testing.

At this point, the proof-testing of pressure vessel 12 is completed. Whether pressure vessel 12 has passed the proof-testing depends upon the differences between the first level and the second and third levels. These differences indicate the amount of deformation of pressure vessel 12 under dynamic and static conditions. If too large a deformation of pressure vessel 12 has occurred as a result of the proof-testing, this indicates a weakness in the walls of pressure vessel 12, which may indicate that filling vessel 12 with pressurized gas could cause an explosion.

For those pressure vessels 12 which have passed the proof-testing, the next step in the process is draining of the water contained within the pressure vessel 12, and the flushing of pressure vessel 12 with air to dry the interior of pressure vessel 12. Once this has been completed, pressure vessel 12 is ready to be filled with the gas (whether it be air, nitrogen, oxygen, or some other gas).

In conclusion, the present invention provides an extremely simple yet effective apparatus and method for proof-testing of pressure vessels. Unlike the prior art devices, which have involved permanent installations which are extremely extensive, the present invention is a low-cost, portable, and easy-to-use unit which is well within the budget of shipyards, fire departments, and other organizations which have in the past sent out their pressure vessels for proof-testing. The availability of a low-cost, easy-to-use and portable unit allows proof-testing to be performed more regularly, and at much lower cost than has been the case in the prior art.

Although the present invention has been described with reference to preferred embodiments, workers skilled in the art will recognize that changes may be made in form and detail without departing from the spirit and scope of the invention.

What is claimed is:

1. A hydrostatic test stand for proof-testing of a pressure vessel in which the pressure vessel is filled with water, is supplied with further water under pressure to pressurize the vessel to a predetermined elevated pressure, and in which a measure of expansion of the vessel is obtained, the test stand comprising:
    a coupling for connection to a port of the pressure vessel;
    a transfer cylinder having first and second fluid passages at first and second ends, respectively;
    a piston movable within the transfer cylinder between the first and second ends to define a first variable volume between the piston and the first end for containing water and a second volume between the piston and the second end for containing hydraulic fluid;
    a spring within the cylinder for applying a bias force to the piston to urge the piston toward a home position at the second end in whch the first volume is a maximum and the second volume is a minimum;
    a graduated cylinder for containing a column of water having a level which varies during the testing and which provides a measure of expansion of the pressure vessel;
    a first control valve connected between the graduated cylinder and the first fluid passage;
    a second control valve connected between the coupling and the first fluid passage;
    pressure sensor means for measuring water pressure supplied to the pressure vessel;
    a reservoir for containing hydraulic fluid;
    booster pump means for pumping hydraulic fluid under pressure from the reservoir to the second fluid passage; and
    a booster pump valve connected between the booster pump and the second fluid passage, the booster pump valve having a first state which prevents oil in the second volume from returning to the reservoir and a second state which permits hydraulic fluid in the second volume to return to the reservoir.

2. The hydrostatic test stand of claim 1 and further comprising:
    a cage for surrounding the pressure vessel during testing.

3. The hydrostatic test stand of claim 2 and further comprising:
    a movable cart for supporting the cage, the transfer cylinder, the reservoir, and the booster pump.

4. The hydrostatic test stand of claim 3 wherein the cage comprises a first semicylindrical shell attached to a side of the cart, a second semicylindrical shell hingedly connected to the first shell, and latch means for holding the second shell in a closed position when the pressure vessel is positioned within a cavity defined by the first and second shells.

5. The hydrostatic test stand of claim 1 wherein the piston carries a first set of sealing and cleaning rings at a first end and carries a second set of sealing and cleaning rings at a second end.

6. The hydrostatic test stand of claim 5 wherein the transfer cylinder has a bore with a surface of approximately a 16 micro-finish.

7. The hydrostatic test stand of claim 1 wherein the spring is a helical compression spring positioned in the transfer cylinder between the first end of the transfer cylinder and piston.

8. A method of proof-testing a pressure vessel comprising:
    filling the pressure vessel with water through a port of the pressure vessel;
    connecting the port to a test system which includes:
        a coupling for connection to the port of the pressure vessel;
        a transfer cylinder having first and second fluid passages at first and second ends, respectively;
        a piston movable within the transfer cylinder between the first and second ends to define a first variable volume between the piston and the first end for containing water and a second volume between the piston and the second end for containing hydraulic fluid;
        a spring within the cylinder for applying a bias force to the piston to urge the piston toward a home position at the second end in which the first volume is a maximum and the second volume is a minimum;
        a graduated cylinder for containing a column of water having a level which varies during the testing and which provides a measure of deformation of the pressure vessel;
        a first control valve connected between the graduated cylinder and the first fluid passage;
        a second control valve connected between the coupling and the first fluid passage;

a pressure sensor for measuring water pressure in the cylinder;

a reservoir for containing hydraulic fluid;

a booster pump for pumping hydraulic fluid under pressure from the reservoir to the second fluid passage; and a booster pump valve connected between the booster pump and the second fluid passage, the booster pump valve having a closed state which prevents oil in the second volume from returning to the reservoir and an open state which permits hydraulic fluid in the second volume to return to the reservoir;

opening the first and second control valves and the booster pump valve;

filling the graduated cylinder with water until a predetermined first level is attained;

closing the first control valve;

closing the booster pump valve;

actuating the booster pump to pump hydraulic fluid from the reservoir to the second fluid passage to cause expansion of the second volume until a predetermined pressure is attained as indicated by the pressure sensor;

closing the second control valve;

opening the booster pump valve;

opening the first control valve to permit water to flow from the graduated cylinder into the first volume to permit the piston to return to the home position, a difference between the first level of the column of water in the graduated water cylinder and a second level of the column after the piston has returned to the home position being an indication of volumetric expansion of the pressure vessel under the predetermined pressure; and opening the second control valve to permit water to flow from the pressure vessel into the graduated cylinder, a difference between the first level and a third level attained after the second control valve is opened being an indication of permanent expansion of the pressure vessel as a result of the predetermined pressure.

* * * * *